United States Patent [19]

Eury et al.

[11] Patent Number: 5,605,696
[45] Date of Patent: Feb. 25, 1997

[54] DRUG LOADED POLYMERIC MATERIAL AND METHOD OF MANUFACTURE

[75] Inventors: Robert P. Eury, Cupertino; Darlene Garguilo, Fremont; Plaridel Villareal, San Jose, all of Calif.

[73] Assignee: Advanced Cardiovascular Systems, Inc., Santa Clara, Calif.

[21] Appl. No.: 413,475

[22] Filed: Mar. 30, 1995

[51] Int. Cl.[6] .............................. A61F 2/02; A61F 2/06; A61K 9/50; B01J 13/02
[52] U.S. Cl. ........................ 424/423; 424/501; 264/4.3; 623/1
[58] Field of Search ................................ 424/486, 423, 424/501; 264/4.3; 623/1

[56] References Cited

U.S. PATENT DOCUMENTS

| | | | |
|---|---|---|---|
| 4,299,613 | 11/1981 | Cardarelli | 71/64 |
| 4,346,028 | 8/1982 | Griffith | 524/417 |
| 4,400,374 | 8/1983 | Cardarelli | 424/78 |
| 4,441,215 | 4/1984 | Kaster | 623/1 |
| 4,633,873 | 1/1987 | Dumican et al. | 128/334 |
| 4,718,907 | 1/1988 | Karwoski et al. | 623/12 |
| 4,768,507 | 9/1988 | Fischell et al. | 128/303 |
| 4,879,135 | 11/1989 | Greco et al. | 623/66 |
| 4,902,290 | 2/1990 | Fleckenstein et al. | 623/1 |
| 5,059,211 | 10/1991 | Stack et al. | 606/108 |
| 5,062,829 | 11/1991 | Pryor et al. | 424/438 |
| 5,084,065 | 1/1992 | Weldon et al. | 623/12 |
| 5,085,755 | 4/1992 | Daniels et al. | 424/426 |
| 5,104,403 | 4/1992 | Brotzu et al. | 623/1 |
| 5,156,623 | 10/1992 | Hakamatsuka et al. | 604/890.1 |
| 5,163,951 | 11/1992 | Pinchuk et al. | 623/1 |
| 5,180,366 | 1/1993 | Woods | 604/96 |
| 5,197,977 | 3/1993 | Hoffman, Jr. et al. | 623/1 |
| 5,234,456 | 8/1993 | Silvestrini | 604/96 |
| 5,234,457 | 8/1993 | Anderson | 606/198 |
| 5,236,447 | 8/1993 | Kubo et al. | 623/1 |
| 5,279,594 | 1/1994 | Jackson | 604/103 |

(List continued on next page.)

FOREIGN PATENT DOCUMENTS

WO91/17789 5/1991 WIPO.
WO93/06792 4/1993 WIPO.

OTHER PUBLICATIONS

Eury, *Chemical Abstracts*, vol. 121, #7810, 1993.
Eury, *Chemical Abstracts*, vol. 121, #213062, 1992.
"Totally Resorbable High–Strength Composite Material," by Benjamin S. Kelley, Richard L. Dunn and Robert A. Casper, *Advances in Biomedical Polymers* Edited by Charles G. Gebelein.
"A View of Vascular Stents" by Richard A. Schatz, M.D. from the Arizona Heart Institute Foundation, Phoenix, Arizona (1988).
"Fiber–Reinforced Absorbable Composite for Orthopedic Surgery" by R. A. Casper, B. S. Kelley, R. L. Dunn, A. G. Potter, and D. N. Ellis in *Polymeric Materilas Science and Engineering*, Proceedings of the ACS DivisiofPlyei Mtra: Science and Engineering, vol. 53, Fall Meeting 1985.

*Primary Examiner*—Carlos Azpuru
*Attorney, Agent, or Firm*—Fulwider Patton Lee & Utecht

[57] ABSTRACT

The drug loaded polymeric material containing a therapeutic drug can be applied to a structure of an intravascular stent. A therapeutically effective amount of a therapeutic drug is incorporated into such a layer of polymeric material, without significantly increasing the thickness of the stent, to avoid interfering with the function of the stent. The drug loaded polymer coating of the stent can formed to include pores, can be multi-layered to permit the combination of a plurality of different drug containing materials in a single stent, and can include a rate controlling membrane to allow for controlled retention and delivery of selected drugs within the affected blood vessel upon implantation. The layer of polymeric material is manufactured by combining the selected polymeric material with a relatively high loading of the therapeutic drug in a thermal process, such as coextrusion of the therapeutic drug with the polymeric material. The therapeutic drug is dispersed and incorporated into the polymer as small particles, preferably having a maximum cross-sectional dimension of 10 microns.

39 Claims, 1 Drawing Sheet

U.S. PATENT DOCUMENTS

| | | | |
|---|---|---|---|
| 5,290,271 | 3/1994 | Jernberg | 604/891.1 |
| 5,342,348 | 8/1994 | Kaplan | 623/1 |
| 5,342,621 | 8/1994 | Eury | 424/423 |
| 5,356,433 | 10/1994 | Rowland et al. | 623/11 |
| 5,380,299 | 1/1995 | Fearmot e tal. | 604/265 |
| 5,383,925 | 1/1995 | Schmitt | 600/36 |
| 5,385,580 | 1/1995 | Schmitt | 623/1 |

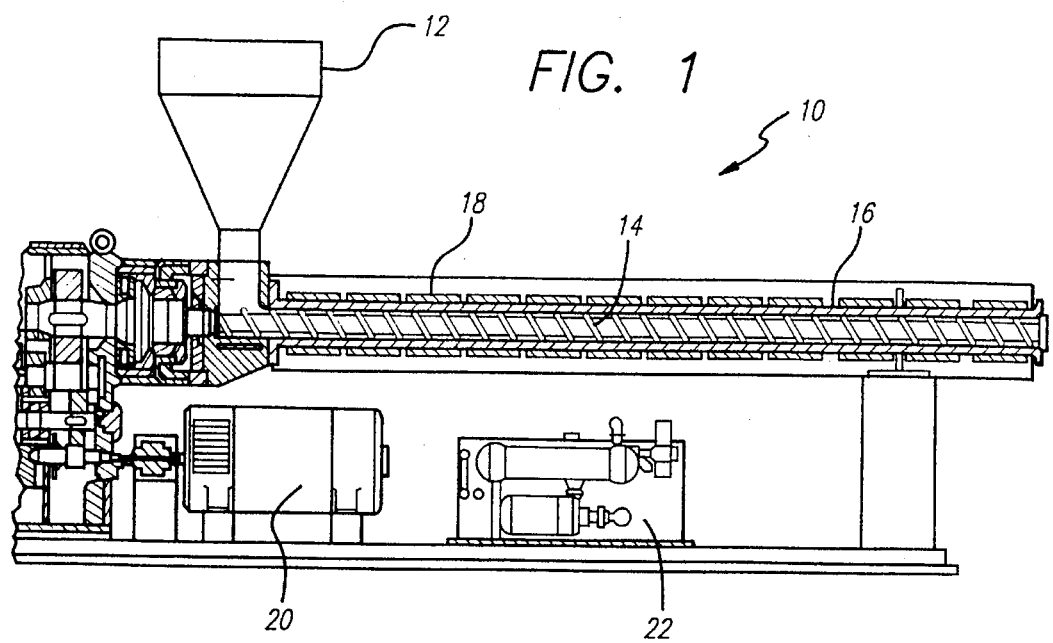
FIG. 1
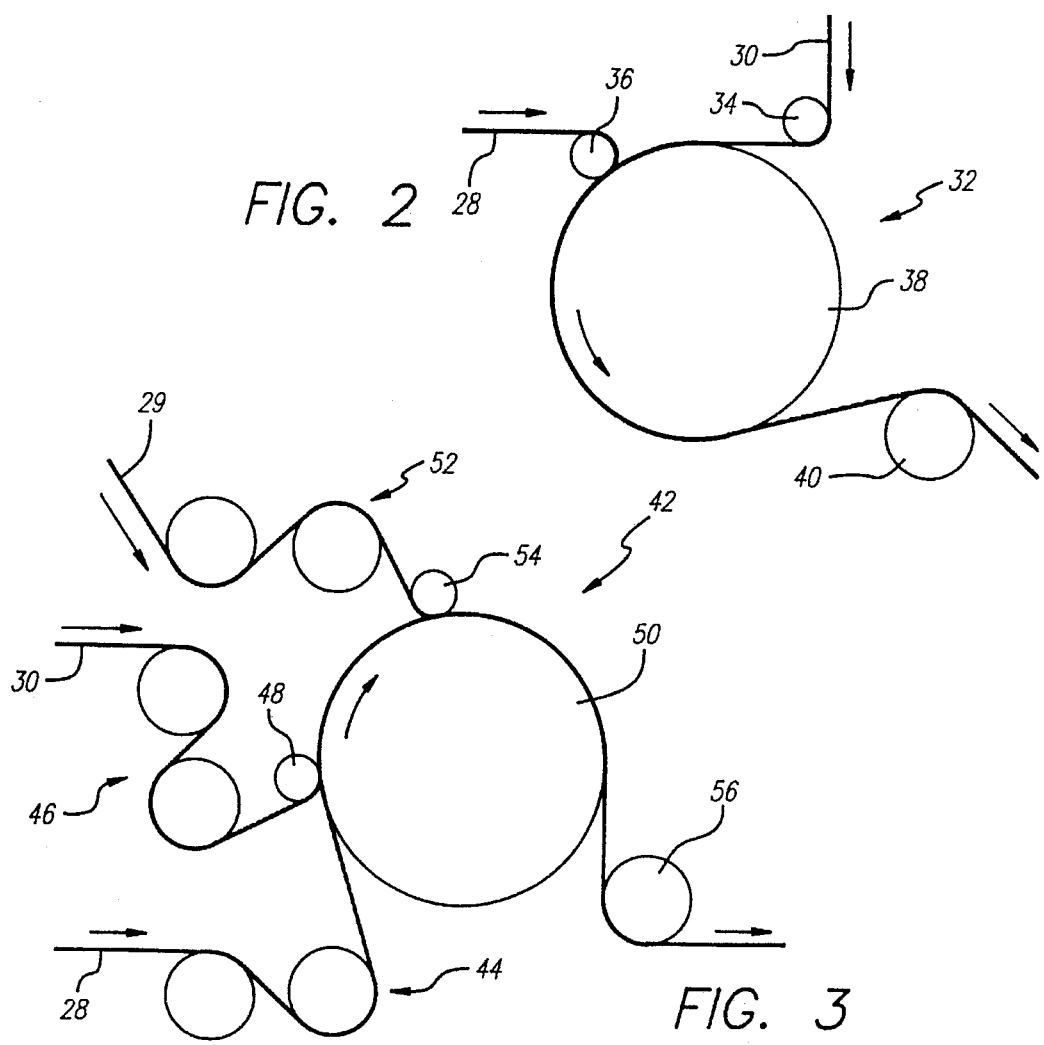
FIG. 2
FIG. 3

DRUG LOADED POLYMERIC MATERIAL AND METHOD OF MANUFACTURE

BACKGROUND OF THE INVENTION

1. Field of the Invention

This invention relates generally to expandable intraluminal vascular grafts, generally referred to as stents, and more particularly concerns stents coated with a polymer component capable of carrying and releasing therapeutic drugs, and a method of incorporating therapeutic drugs into the polymer component of such stents.

2. Description of Related Art

Systemic administration of some therapeutic pharmaceutical drugs in order to provide an efficacious concentration at a localized area of interest can produce serious systemic side effects. Local administration of a therapeutic drug can be significantly more effective and produce fewer side effects than systemic delivery, particularly for anticoagulants used for preventing thrombosis of a coronary stent, and cytostatic agents applied for reducing postangioplasty proliferation of vascular tissue, which is a factor in restenosis after angioplasty.

There has thus been a need in modern medicine for techniques for local delivery of therapeutic drugs. In one technique, catheters have been used to deliver therapeutic drugs in a solution used to bathe the tissue for a short period of time, which is effective for administration of thrombolytic drugs, or to inject the drug solution into the tissue surrounding the area of interest. However, the therapeutic effect of drugs delivered by this method is generally relatively short, as the drugs are commonly easily eliminated from the delivery site.

Therapeutic drugs have been incorporated into relatively permanent structures for longer term delivery of the drugs at the site of interest. For example, extravascular wraps having a relatively large quantity of a drug in a bandage structure can be applied around the exterior of an artery. Although work in animals has shown that this technique is effective for local anticoagulation with heparin, it has limited practical utility in human beings, since an invasive operation is required to place the extravascular wrap at the site of interest.

In another technique, coatings of therapeutic drugs have been applied to stents in order to provide sustained delivery of the drugs at the site of interest. However, while coatings thick enough to provide a therapeutically effective amount of the drug can severely compromise the function of the stent, very thin coatings that do not impede the function of the stent, such as heparin coatings with a thickness of several microns, typically do not deliver a therapeutically effective amount of the drug.

It would be desirable to provide a method of incorporating a therapeutically effective amount of a therapeutic drug into an intravascular layer of polymeric material which can be applied to a relatively permanent intravascular device, such as a stent, that does not require an invasive operation for placement of the device, in a way that would not interfere with the functioning of the stent. The present invention meets these needs.

SUMMARY OF THE INVENTION

Briefly, and in general terms, the present invention provides for a polymeric material containing a therapeutic drug for application to a structure of an intravascular stent, and a method of incorporating a therapeutically effective amount of a therapeutic drug into a polymeric material for application to the structure of an intravascular stent, which when applied to the structure of the stent will not significantly increase the thickness of the stent, to avoid interfering with the function of the stent.

Accordingly, the present invention provides for a polymeric material containing a therapeutic drug, for application to a thin reinforcement or structural member of the stent on at least one side, for carrying and releasing the therapeutic drug. The thin reinforcement provides the structural strength required for maintaining the patency of the vessel in which the stent is placed, and the polymer coating provides the stent with the capacity for carrying and releasing therapeutic drugs at the location of the stent of the vessel in which the stent is placed. The polymer coating can be formed to include pores or to contain a material which will dissolve or degrade to form pores in the polymeric material, can be multi-layered to permit the combination of a plurality of different drug containing materials in a single stent, and can include a rate controlling membrane to allow for controlled retention and delivery of selected drugs within the affected blood vessel upon implantation. Depending upon the construction and lamination of the stent, drugs can be released simultaneously or sequentially, on the exterior surface of the stent to a blood vessel wall, and directly into the bloodstream, as desired.

The present invention also provides for a method of incorporating a therapeutic drug into a polymeric material. In one preferred embodiment of the method of the invention, a layer of polymeric material is manufactured by combining the selected polymeric material with a relatively high loading of the therapeutic drug in a thermal process, such as coextrusion of the therapeutic drug with the polymeric material, for example, although other thermal processes such as molding or calendaring may also be suitable. The polymeric material is preferably selected to have a relatively low processing temperature, where the drug of interest is thermally unstable. In another preferred embodiment of the method of the invention, particularly where the drug of interest is thermally unstable and a low temperature processing polymer is not suitable, the layer of the selected polymeric material can be formed by solvent casting or coating the polymeric material with the selected therapeutic drug. In either a thermal process, such as coextrusion, or a low or ambient temperature process, such as solvent casting, the therapeutic drug can be dispersed and incorporated into a polymer as small particles, preferably having a maximum cross-sectional dimension of about 10 microns.

These and other aspects and advantages of the invention will become apparent from the following detailed description, and the accompanying drawings, which illustrate by way of example aspects of the invention.

BRIEF DESCRIPTION OF THE DRAWINGS

FIG. 1 is a cross-sectional view of an extrusion apparatus for use in combining a therapeutic drug with a polymer component of a stent according to the method of the invention;

FIG. 2 is a diagrammatic view of a laminating apparatus that can be used for laminating the reinforcement member of the stent on one side with a drug loaded polymeric film; and FIG. 3 is a diagrammatic view of a lamination apparatus that can be used for laminating the reinforcement member of the stent on two sides with a drug loaded polymeric film.

DETAILED DESCRIPTION OF THE PREFERRED EMBODIMENTS

Local administration of therapeutic drugs to avoid the serious side effects that can result from systemic administration of some therapeutic drugs can result in limitation of the effective duration of the drug to a relatively short period of time, due to elimination of the therapeutic drug from the delivery site. Administration of therapeutic drugs to a blood vessel by a relatively permanent intravascular device to provide a longer effective duration of localized drug therapy also poses the problem of providing a therapeutically effective amount of the drug without substantially increasing the thickness of the device, which could otherwise injure or block the vessel.

The invention is accordingly embodied in a polymeric material containing a therapeutically effective amount of a therapeutic drug that can be combined with the reinforcement structure of an intravascular stent, and a method of incorporating the therapeutic drug into the polymeric material and forming the polymeric material as a thin layer containing a therapeutically effective amount of the therapeutic drug, to be incorporated in the stent without significantly increasing the thickness of the stent.

As is illustrated in the drawings, in one preferred embodiment, a selected therapeutic drug is preferably intimately mixed with the selected polymeric material so as to uniformly disperse the therapeutic drug in the polymeric material. The specific method of uniformly dispersing the therapeutic drug in the polymer can vary, and depends upon the stability of the therapeutic drug to thermal processing. However, in a preferred embodiment, the therapeutic drug is uniformly dispersed in the polymeric material by coextruding small solid particles of the selected therapeutic drug with the selected polymeric material, as is illustrated in FIG. 1. Such an extrusion apparatus 10 typically includes a hopper into which the polymeric material and small particles of the selected therapeutic drug are added together, and into which a porosigen can also be added, if desired. The extruder also typically includes a lead screw 14 that drives and intimately mixes the ingredients together, to uniformly disperse the small particles of the therapeutic drug, and if desired, a porosigen as well, in the polymeric material. The barrel 16 of the extruder is preferably heated by temperature controlled heaters 18 surrounding the barrel in stages. A motor 20 and associated gears are provided to drive the lead screw, and a cooling system 22 is also typically provided. This method of intimately mixing the therapeutic drug and polymeric material can yield a relatively high and uniformly distributed loading of the therapeutic drug in the polymer. While a loading of the therapeutic drug is currently preferably no more than about 40% by weight, depending upon the specific application and interaction of the polymer with the drug, drug loadings as high as 70% by weight have been achieved by this method. The drug loaded polymer can be extruded into an appropriate shape, or can be subsequently calendared to produce a drug loaded polymer film having a smooth surface, with the therapeutic drug uniformly distributed in the film.

The selected therapeutic drug can, for example, be anticoagulant antiplatelet or antithrombin agents such as heparin, D-phe-pro-arg-chloromethylketone (synthetic antithrombin), dipyridamole, hirudin, recombinant hirudin, thrombin inhibitor (available from Biogen), or c7E3 (an antiplatelet drug from Centocore); cytostatic or antiproliferative agents such as angiopeptin (a somatostatin analogue from Ibsen), angiotensin converting enzyme inhibitors such as Captopril (available from Squibb), Cilazapril (available from Hoffman-LaRoche), or Lisinopril (available from Merk); calcium channel blockers (such as Nifedipine), colchicine, fibroblast growth factor (FGF) antagonists, fish oil (omega 3-fatty acid), low molecular weight heparin (available from Wyeth, and Glycomed), histamine antagonists, Lovastatin (an inhibitor of HMG-CoA reductase, a cholesterol lowering drug from Merk), methotrexate, monoclonal antibodies (such as to PDGF receptors), nitroprusside, phosphodiesterase inhibitors, prostacyclin and prostacyclin analogues, prostaglandin inhibitor (available from Glaxo), Seramin (a PDGF antagonist), serotonin blockers, steroids, thioprotease inhibitors, and triazolopyrimidine (a PDGF antagonist). Other therapeutic drugs which may be appropriate include alphainterferon and genetically engineered epithelial cells, for example.

The particles of the desired therapeutic drug are preferably formed by air milling of crystals of the therapeutic drug to form microgranules of the therapeutic drug. This method is preferred because it typically produces no heat and generally does not lead to contamination of the therapeutic drug. The particles of the desired therapeutic drug can also be formed by recrystallization, ball milling or grinding, where generation of heat and possible contamination are closely controlled.

The particles of the desired therapeutic drug are preferably formed to have a maximum cross-sectional dimension of about 10 microns. An average particle size of less than 10 microns, and a uniform distribution of the particles of the therapeutic drug in the polymeric material, are critical to provision of a therapeutically effective amount of the therapeutic drug in the layer of polymeric material to be applied to the structure of the stent, since the layer of polymeric material typically can be as thin as 25 microns. The size and distribution of the particles of the therapeutic drug can also affect the physical properties of the polymer.

In a preferred aspect of the method of the invention, the polymeric material in which the therapeutic drug is incorporated has a relatively low processing temperature, such as polycaprolactone, having a processing temperature of approximately 80° C., poly(ethylene-co-vinyl acetate) or poly(vinyl acetate), having processing temperatures of approximately 100° C., or silicone gum rubber,,having a processing temperature of about 40° C., for example. Other polymers having similar relatively low processing temperatures may also be suitable. Other polymers which may be suitable include non-degradable polymers capable of carrying and delivering therapeutic drugs, and biodegradable, bioabsorbable polymers capable of carrying and delivering therapeutic drugs, such as poly-DL-lactic acid (DL-PLA), and poly-L-lactic acid (L-PLA), polyorthoesters, polyiminocarbonates, aliphatic polycarbonates, and polyphosphazenes.

Alternatively, the therapeutic drug can be compounded with the polymer by calendaring the ingredients, such as in a two roll mill, for example. This method can also yield a relatively high and uniformly distributed loading of the therapeutic drug in the polymer.

A porosigen can also be incorporated in the drug loaded polymer by adding the porosigen to the polymer along with the therapeutic drug to form a porous, drug loaded polymeric membrane. A porosigen is defined herein for purposes of this application as any moiety, such as microgranules of sodium chloride, lactose, or sodium heparin, for example, which will dissolve or otherwise be degraded when immersed in body fluids to leave behind a porous network in the polymeric material. The pores left by such porosigens can typically be a large as 10 microns. The pores formed by porosigens such as polyethylene glycol (PEG), polyethylene oxide/polypropylene oxide (PEO/PPO) copolymers, for example, can also be smaller than one micron, although other similar materials which form phase separations from the continuous drug loaded polymeric matrix and can later be leached out by body fluids can also be suitable for forming pores smaller than one micron. While it is currently preferred to apply the polymeric material to the structure of a stent while the therapeutic drug and porosigen material are contained within the polymeric material, to allow the porosigen to be dissolved or degraded by body fluids when the stent is placed in a blood vessel, alternatively the porosigen can be dissolved and removed from the polymeric material to form pores in the polymeric material prior to placement of the polymeric material combined with the stent within a blood vessel.

If desired, a rate-controlling membrane can also be applied over the drug loaded polymer, to limit the release rate of the therapeutic drug. Such a rate-controlling membrane can be useful for delivery of water soluble substances where a nonporous polymer film would completely prevent diffusion of the drug. The rate-controlling membrane can be added by applying a coating from a solution, or a lamination, as described previously. The rate-controlling membrane applied over the polymeric material can be formed to include a uniform dispersion of a porosigen in the rate-controlling membrane, and the porosigen in the rate-controlling membrane can be dissolved to leave pores in the rate-controlling membrane typically as large as 10 microns, or as small as 1 micron, for example, although the pores can also be smaller than 1 micron. The porosigen in the rate-controlling membrane can be, for example, sodium chloride, lactose, sodium heparin, polyethylene glycol, polyethylene oxide/polypropylene oxide copolymers, and mixtures thereof.

The drug loaded polymer can be laminated to the surface of a stent. The inner reinforcement structure to which the drug load polymer is laminated is preferably formed from a thin sheet of metal, such as stainless steel, although other metals such as platinum-iridium alloy, molybdenum-rhenium alloy, tantalum, gold, combinations thereof and other similar materials that may also be suitable. The inner metal reinforcement structure of the stent is preferably laminated with polymer films on each side, with at least one coating of a polymer film. Alternatively, the reinforcement structure can also be coated on one side, if desired. At least one laminating polymeric film capable of absorbing and releasing therapeutic drugs is placed on at least one side of the reinforcement member of the stent, and the laminating polymeric film is heated to its appropriate processing temperature to bond the laminating polymeric film to the surface of the inner stent member to form a laminated stent member.

When the structural reinforcement member 30 of the stent is to be laminated on one side only, the reinforcement member and polymer film can be bonded by a typical two-ply fusion lamination system 32, as is illustrated in FIG. 2. The two ply laminating stack typically includes an idler roll 34 receiving a sheet of the reinforcement members 30, and a lay-on roll 36 receiving the drug loaded polymeric film 28. The reinforcement member 30 and drug loaded polymeric film 28 are pressed into intimate contact between the lay-on roll and the heating and combining drum 38, and can be heated by the drum and take-off heat roll 40, where the reinforcement member and drug loaded film laminate can be utilized for further processing in making the drug loaded stent.

When the reinforcement member is to be laminated on both sides, the reinforcement member 30 and drug loaded polymeric film layers 28, 29 can be bonded together by typical three-ply fusion lamination rolls, as is illustrated in FIG. 3. Such a three-ply fusion lamination system 42 can typically include a first preheat roll system 44 for receiving and preheating one drug loaded polymeric film 28, a second preheat roll system 46 for receiving and preheating the sheet of reinforcement members 30, and a lay-on roll 48 for pressing the reinforcement member and first drug loaded polymeric laminating film together in intimate contact against the heating and combining drum 50. A third preheat roll system 52 can be provided for receiving and preheating the second drug loaded polymeric laminating film 29, and a lay-on roll 54 presses the second drug loaded polymeric laminating film and reinforcement member together in intimate contact against the drum. The reinforcement member and two layers of laminating film can be further heated by the drum and take-off heat roll 56, and removed for further processing in making the drug loaded stent. Other laminating systems that combine the reinforcement member with one or more of the drug loaded polymeric laminating films may also be suitable. Alternatively, the polymeric film can be applied by solvent casting, or by adhering the film to the surface of the inner stent member with a biocompatible adhesive.

Any excess polymer extending beyond the desired edges of orifices or the outside edges of the stent is preferably removed, typically by cutting with a laser (not shown), such as a continuous $CO_2$ laser, a pulsed YAG laser, or an excimer laser, for example, although the excess polymer can also be removed by stamping and the like.

It has thus been demonstrated that the invention provides for a polymeric material containing a therapeutically effective amount of a therapeutic drug that can be combined with a reinforcement structure of an intravascular stent, and a method of incorporating the therapeutic drug into the polymeric material for combination with the stent, and for forming the polymeric material as a thin layer containing a therapeutically effective amount of the therapeutic drug to be incorporated in the stent without significantly increasing the thickness of the stent.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method of incorporating a therapeutically effective amount of a therapeutic drug into a polymeric material for application to an intravascular stent, the method comprising the steps of:

forming solid particles of a therapeutic drug to have a maximum cross-sectional dimension of about 10 microns;

uniformly dispersing said solid particles of said therapeutic drug in said polymeric material such that said particles of said therapeutic drug form up to 70% by weight of the total weight of the therapeutic drug and the polymeric material; and uniformly dispersing a porosigen in said polymeric material together with said therapeutic drug, said porosigen being selected from the group consisting of sodium chloride, lactose, sodium heparin, polyethylene glycol, copolymers of polyethylene oxide and polypropylene oxide, and mixtures thereof.

2. The method of claim 1, wherein said step of forming solid particles of said therapeutic drug comprises air milling crystals of said therapeutic drug.

3. The method of claim 1, wherein said step of forming solid particles of said therapeutic drug comprises recrystallizing crystals of said therapeutic drug.

4. The method of claim 1, wherein said step of forming solid particles of said therapeutic drug comprises ball milling crystals of said therapeutic drug.

5. The method of claim 1, wherein said step of forming solid particles of said therapeutic drug comprises grinding crystals of said therapeutic drug.

6. The method of claim 1, wherein said therapeutic drug is selected from the group consisting of heparin, D-phe-pro-arg-chloromethylketone, dipyridamole, hirudin, recombinant hirudin, thrombin inhibitor, angiopeptin, angiotensin converting enzyme inhibitors, calcium channel blockers, colchicine, fibroblast growth factor antagonists, fish oil, omega 3-fatty acid, low molecular weight heparin, histamine antagonists, inhibitors of HMG-CoA reductase, methotrexate, monoclonal antibodies, nitroprusside, phosphodiesterase inhibitors, prostacyclin and prostacyclin analogues, prostaglandin inhibitor, PDGF antagonists, serotonin blockers, steroids, thioprotease inhibitors, triazolopyrimidine, alpha-interferon, and genetically engineered epithelial cells, and mixtures thereof.

7. The method of claim 1, wherein said polymeric material has a relatively low thermal processing temperature.

8. The method of claim 1, wherein said polymeric material has a thermal processing temperature of not more than approximately 100° C.

9. The method of claim 1, wherein said polymeric material is selected from the group consisting of polycaprolactone, poly(ethylene-co-vinyl acetate), poly(vinyl acetate), silicone gum rubber, poly-DL-lactic acid (DL-PLA), poly-L-lactic acid (L-PLA), polyorthoesters, polyiminocarbonates, aliphatic polycarbonates, polyphosphazenes, and mixtures thereof.

10. The method of claim 1, wherein said particles of said therapeutic drug comprise up to 70% by weight of the total weight of the therapeutic drug and the polymeric material.

11. The method of claim 1, wherein said step of uniformly dispersing said solid particles of said therapeutic drug in said polymeric material comprises coextruding said particles of said therapeutic drug and said polymeric material.

12. The method of claim 1, wherein said step of uniformly dispersing said solid particles of said therapeutic drug in said polymeric material comprises calendaring said particles of said therapeutic drug and said polymeric material together.

13. The method of claim 1, wherein said step of uniformly dispersing said solid particles of said therapeutic drug in said polymeric material comprises solvent casting said particles of said therapeutic drug together with said polymeric material.

14. The method of claim 1, wherein said step of uniformly dispersing a porosigen in said polymeric material together with said therapeutic drug comprises coextruding said porosigen together with said therapeutic drug and said polymeric material.

15. The method of claim 1, further including the step of dissolving said porosigen in said polymeric material to leave pores in said polymeric material.

16. The method of claim 15, wherein said pores have a maximum cross-sectional dimension of about 10 microns.

17. The method of claim 15, wherein said pores have a maximum cross-sectional dimension of about one micron.

18. The method of claim 1, further including the step of applying a rate-controlling membrane over said polymeric material to control the release rate of said therapeutic drug from said polymeric material.

19. The method of claim 18, wherein said step of applying a rate-controlling membrane over said polymeric material comprises forming said rate-controlling membrane to include a uniform dispersion of a porosigen in said rate-controlling membrane.

20. The method of claim 19, further including the step of dissolving said porosigen in said rate-controlling membrane to leave pores in said rate-controlling membrane.

21. The method of claim 19, wherein said porosigen in said rate-controlling membrane is selected from the group consisting of sodium chloride, lactose, sodium heparin, polyethylene glycol, polyethylene oxide/polypropylene oxide copolymers, and mixtures thereof.

22. The method of claim 1, further including the step of forming said polymeric material containing said therapeutic drug as a sheet at least about 25 microns thick.

23. The method of claim 22, further including the step of laminating said sheet of polymeric material containing said therapeutic drug to an intravascular stent structure.

24. The method of claim 23, further including the step of removing excess polymeric material laminated to said intravascular stent structure.

25. A polymeric material containing a therapeutic drug for application to an intravascular stent for carrying and delivering said therapeutic drug within a blood vessel in which said intravascular stent is placed, comprising:

a polymeric material having a thermal processing temperature no greater than about 100° C;

particles of a therapeutic drug incorporated in said polymeric material; and a porosigen uniformly dispersed in said polymeric material, said porosigen being selected from the group consisting of sodium chloride, lactose, sodium heparin, polyethylene glycol, copolymers of polyethylene oxide and polypropylene oxide, and mixtures thereof.

26. The polymeric material of claim 25, wherein said polymeric material is selected from the group consisting of polycaprolactone, poly(ethylene-co-vinyl acetate), poly(vinyl acetate), silicone gum rubber, poly-DL-lactic acid (DL-PLA), poly-L-lactic acid (L-PLA), polyorthoesters, polyiminocarbonates, aliphatic polycarbonates, polyphosphazenes, and mixtures thereof.

27. The polymeric material of claim 25, wherein said particles of said therapeutic drug can have a maximum cross-sectional dimension of up to 50 microns.

28. The polymeric material of claim 25, wherein said therapeutic drug is a drug selected from the group consisting of heparin, D-phe-pro-arg-chloromethylketone, dipyridamole, hirudin, recombinant hirudin, thrombin inhibitor, angiopeptin, angiotensin converting enzyme inhibitors, calcium channel blockers, colchicine, fibroblast growth factor antagonists, fish oil, omega 3- fatty acid, low molecular weight heparin, histamine antagonists, inhibitors of HMG-CoA reductase, methotrexate, monoclonal antibodies, nitroprusside, phosphodiesterase inhibitors, prostacyclin and prostacyclin analogues, prostaglandin inhibitor, PDGF antagonists, serotonin blockers, steroids, thioprotease inhibitors, triazolopyrimidine, alpha-interferon, and genetically engineered epithelial cells, and mixtures thereof.

29. The polymeric material of claim 25, wherein said particles of said therapeutic drug comprise up to 70% by weight of the total weight of the therapeutic drug and the polymeric material.

30. The polymeric material of claim 25, wherein said particles of said therapeutic drug comprise up to 40% by weight of the total weight of the therapeutic drug and the polymeric material.

31. The polymeric material of claim 25, wherein said polymeric material comprises a surface defining pores with a maximum cross-sectional dimension of less than about 10 microns.

32. The polymeric material of claim 25, further including a rate-controlling membrane.

33. The polymeric material of claim 32, wherein said rate-controlling membrane is formed to include a uniform distribution of a porosigen, said porosigen being selected from the group consisting of sodium chloride, lactose, sodium heparin, polyethylene glycol, polyethylene oxide/polypropylene oxide copolymers, and mixtures thereof.

34. The polymeric material of claim 32, wherein said rate-controlling membrane comprises a surface defining pores with a maximum cross-sectional dimension of about ten microns.

35. The polymeric material of claim 32, wherein said rate-controlling membrane comprises a surface defining pores with a maximum cross-sectional dimension of about one micron.

36. The polymeric material of claim 25, wherein said polymeric material containing said therapeutic drug is formed as a sheet at least about 25 microns thick.

37. The polymeric material of claim 36, wherein said sheet of polymeric material containing said therapeutic drug is further laminated to an intravascular stent structure.

38. A method of incorporating a therapeutically effective amount of a therapeutic drug into a polymeric material for application to an intravascular stent, the method comprising the steps of:

forming solid particles of a therapeutic drug to have a maximum cross-sectional dimension of about 10 microns;

uniformly dispersing said solid particles of said therapeutic drug in said polymeric material such that said particles of said therapeutic drug form up to about 70% by weight of the total weight of the therapeutic drug and the polymeric material;

uniformly dispersing a porosigen in said polymeric material together with said therapeutic drug, said porosigen being selected from the group consisting of sodium chloride, lactose, sodium heparin, polyethylene glycol, copolymers of polyethylene oxide and polypropylene oxide, and mixtures thereof; and applying a rate-controlling membrane over said polymeric material to control the release rate of said therapeutic drug from said polymeric material, said rate controlling membrane being formed of a polymeric material selected from the group consisting of polycaprolactone, poly(ethylene-co-vinyl acetate), poly(vinylacetate), silicone gum rubber, poly-DL-lactic acid (DL-PLA), poly-L-lactic acid (L-PLA), polyorthoesters, polyiminocarbonates, aliphatic polycarbonat polyphosphazenes, and mixtures thereof, said rate controlling membrane polymeric material containing a uniform dispersion of said porosigen.

39. An apparatus containing a therapeutic drug for application to an intravascular stent for carrying and delivering said therapeutic drug within a blood vessel in which said intravascular stent is placed, comprising:

a polymeric material having a thermal processing temperature no greater than about 100° C;

particles of a therapeutic drug incorporated in said polymeric material;

a porosigen uniformly dispersed in said polymeric material, said porosigen being selected from the group consisting of sodium chloride, lactose, sodium heparin, polyethylene glycol, copolymers of polyethylene oxide and polypropylene oxide, and mixtures thereof; and a rate-controlling membrane disposed over said polymeric material to control a rate of release of said therapeutic drug from said polymeric material, said rate controlling membrane being formed of a polymeric material selected from the group consisting of polycaprolactone, poly(ethylene-co-vinyl acetate), poly(vinyl acetate), silicone gum rubber, poly-DL-lactic acid (DL-PLA), poly-L-lactic acid (L-PLA), polyorthoesters, polyiminocarbonates, aliphatic polycarbonates, polyphosphazenes, and mixtures thereof, said rate controlling membrane polymeric material containing a uniform dispersion of said porosigen.

* * * * *